US00PP08589P

United States Patent [19]

Stravers

[11] Patent Number: Plant 8,589

[45] Date of Patent: Feb. 8, 1994

[54] GERBERA PLANT: "TERKAROLA"

[75] Inventor: Lambertus J. M. Stravers, Kudelstaart, Netherlands

[73] Assignee: Terra Nigra B.V., Netherlands

[21] Appl. No.: 942,280

[22] Filed: Sep. 9, 1992

[30] Foreign Application Priority Data

May 20, 1988 [NL] Netherlands ..... GRB 854

[51] Int. Cl.[5] ..... A01H 5/00

[52] U.S. Cl. ..... Plt./68.1

[58] Field of Search ..... Plt. 68.1

*Primary Examiner*—James R. Feyrer

*Assistant Examiner*—Elizabeth C. Kemmerer

[57] ABSTRACT

A new and distinct cultivar of Gerbera plant named 'Terkarola', characterized by its semi-double type, a distinctive orange ray floret which is a solid orange throughout, a red-purple disc floret the outermost petaloids of which fade to orange and display yellow stigmas and anthers, orange perianth lobe color and 110 mm overall flower diamter is disclosed.

1 Drawing Sheet

BACKGROUND OF THE INVENTION

The present invention comprises a new and distinct cultivar of *Gerbera Jamesonni,* referred to by the cultivar name 'Terkarola'. 'Terkarola' was originated from a hybridisation program in De Kwakel, The Netherlands in 1984. The female parent was unnamed seedling 83.1, and the male parent was unnamed seedling 81.178. Female parent 83.1 has a higher and earlier production, less petals and a lower overall flower quality, shorter stems, and a red black center. Of the male parent 81.178 is no description available. Both have not been available outside Terra Nigra and aren't registered in the USA. The new cultivar was selected by me from the progeny of the stated parentage on or about November 1984. The first asexual reproduction of 'Terkarola' was accomplished when vegetative cuttings were taken on May 1985 in De Kwakel. The new cultivar is presently being propagated by cuttings and tissue culture. Horticultural examination of selected units initiated November 1986 has demonstrated that the combination of characteristics as herein disclosed for 'Terkarola' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terkarola', which in combination distinguish this Gerbera from its parents and all other varieties of which I am aware:

1. Type: Semi-double.
2. Color of ray floret: Distinctive orange.
3. Color of disc floret: Red-purple.
4. Color of perianthy lobe: Orange.
5. Diameter of flower head: Medium 110 mm.

Of the many commercial cultivars known to me, there is no cultivar similar in comparison to 'Terkarola'. The patent plant 'Terikatir' (U.S. Plant Pat. No. 7,984) appears to be similar to "Terkarola'. However, 'Terikatir' is a Germini type with a diameter of 6.5 cm, has a dark yellow color, with an average flower production of 55 per plant, whereas 'Terkarola' has a flower diameter of 11–12 cm, a distinctive orange color, and an average flower production of 25 per plant.

BRIEF DESCRIPTION OF THE FIGURE OF THE DRAWING

The accompanying photographic drawing shows typical inflorescence and foliage characteristics nearly true as possible. In the following description, color references are made to The Royal Horticultural Society Color Chart (RHS). The color values were determined at 11.30 a.m. on Mar. 31, 1988 under natural light at De Kwakel.

BOTANICAL DESCRIPTION OF THE PLANT

Botanical: *Gerbera jamessonii* cv Terkarola.

1. INFLORESCENCE

A. Capitulum:
- *Form.*—Flat shaped.
- *Type.*—Semi-double.
- *Diameter across face.*—110 mm.

B. Corolla of ray florets:
- *Color (general tonality from a distance of 3 meters).*—Orange.
- *Color (topside).*—RHS 30B/C.
- *Color (bottom).*—RHS 30A.

C. Corolla of disc florets:
- *Color (mature).*—Purple RHS 187A.
- *Color (immature).*—Purple RHS 187A.

D. Reproductive organs:
- *Stigma.*—Yellow RHS 13A.
- *Anthers.*—Brown+dark-red RHS 166B.
- *Pappus.*—Yellow RHS 11C.

PLANT

A. General appearance:
- *Height.*—45 cm.

B. Foliage:
- *Color (abaxial).*—RHS 147A.
- *Color (adaxial).*—RHS 138B.
- *Shape.*—The angle of apex: Right angle. The shape of apex: Pointed. The margin of lobes: Sinuate.

C. Disease resistance: No special disease resistance.

3. OTHER CHARACTERISTICS

The following traits have been repeatedly observed and are determined to be basic characteristics of 'Terkarola', which in combination distinguish this Gerbera as a new and distinct cultivar.

Leaf blade:

*Length.*—Medium (50 cm).

*Width.*—Medium (19 cm).

*Thickness.*—Medium.

*Blistering.*—Stark.

*Pubescence.*—On upper side (midrib excluded) of the leaf blade is medium.

*Depth of cuts or incisions in leaf.*—Basal part: Medium. Central part: Deep. Distal part: Shallow.

*Color.*—Upperside of the leaf blade is medium green (RHS 147A).

*Glossiness on upper side.*—Medium.

*Angle of apex.*—Right angle.

*Shape of apex.*—Pointed.

*Margin of lobes.*—Sinuate.

*Extensions of margin.*—Small.

*Petiole length.*—Medium.

*Petiole anthocyanin coloration.*—Present.

Peduncle:

*Length.*—Medium (70 cm).

*Cross section.*—Round.

*Tendency to fasciation.*—Absent.

*Thickness.*—Medium.

*Strength.*—Strong.

*Pubescence.*—Strong.

*Color.*—Medium green.

*Anthocyanin coloration.*—At base: Weak. At top: Weak.

*Involucral bracts.*—Present.

Flower head:

*Type.*—Semi-double.

*Diameter.*—Medium (approx. 110 mm).

*Involucre.*—Height: Medium (17 mm). Diameter: Medium/Large. Number of bracts: Medium (40). Longitudinal axis of bracts of inner rows: Reflexing. Anthocyanin: Present. Pubescence: Medium.

*Ray florets.*—Number: Medium (55). Shape: Narrow elliptic. Longitudinal axis outer row: Straight to somewhat reflexing. Longitudinal axis inner row: Straight to somewhat reflexing.

*Outer ray florets.*—Cross section: Flat. Length: Medium (43 mm). Width: Broad. Longitudinal folding: Medium. Angle of apex: Obtuse. Shape of apex: Rounded. Incisions of apex: Absent. Length of free petals: Medium. Edge of different color: Absent. Striation: Absent. Claw spot: Present.

Disc florets:

*Diameter.*—Medium.

*Main color perianth lobes.*—Female flowers: red RHS 33A. Male flowers: red RHS 44A. The disc florets are red-purple in the center and fade to orange near the perimeter of the disc floret. The florets near the perimeter of the disc floret display yellow stigmas and anthers.

Reproductive parts:

*Stigma.*—Main color yellow (RHS 13A).

*Anthers.*—Main color brown (RHS 166B). Color of top relative to other parts is lighter. Longitudinal striping: Absent.

*Pappus.*—Main color yellow (RHS 11C). Color of top relative to other parts is darker. Orientation: Level of top relative to closed disc florets is above.

*Fertility.*—Fertility is well; reasonable seed setting.

I claim:

1. A new and distinct cultivar of Gerbera plant named 'Terkarola', as illustrated and described, characterized by its semi-double type, a distinctive orange ray floret which is a solid orange color throughout, a red-purple disc floret the outermost petaloids of which fade to orange and display yellow stigmas and anthers, orange perianth lobe color and 110 mm overall flower diameter.

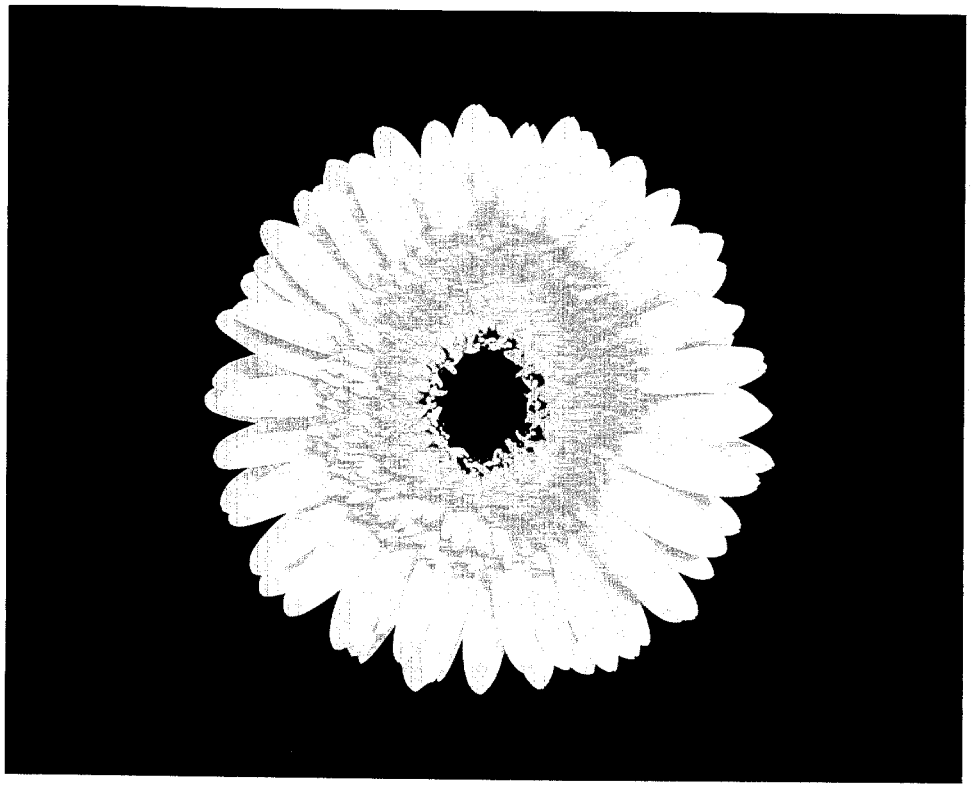

* * * * *